US011554135B2

(12) United States Patent
Rego et al.

(10) Patent No.: US 11,554,135 B2
(45) Date of Patent: *Jan. 17, 2023

(54) METHOD AND APPARATUS FOR USING IODINATED POLYMER AS AN ANTIMICROBIAL AGENT TO MANAGE THE SUPPRESSION AND DISINFECTION OF PATHOGENS

(71) Applicant: Valencide LLC, San Diego, CA (US)

(72) Inventors: Albert Rego, Mission Viejo, CA (US); Lynn R. Detlor, Ramona, CA (US); Aileen Law, Denver, CO (US)

(73) Assignee: VALENCIDE LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/585,431

(22) Filed: Jan. 26, 2022

(65) Prior Publication Data
US 2022/0143076 A1    May 12, 2022

Related U.S. Application Data

(63) Continuation-in-part of application No. 17/141,961, filed on Jan. 5, 2021, now Pat. No. 11,253,623, which is a continuation-in-part of application No. 17/008,341, filed on Aug. 31, 2021, now Pat. No. 11,071,975, which is a continuation-in-part of application No. 16/844,967, filed on Apr. 9, 2020, now Pat. No. 10,758,480, which is a continuation-in-part of application No. 15/711,424, filed on Sep. 21, 2017, now Pat. No. 10,709,819.

(51) Int. Cl.
*A61K 31/755* (2006.01)
*A61K 9/00* (2006.01)
*A61L 2/23* (2006.01)
*A61L 101/46* (2006.01)

(52) U.S. Cl.
CPC .......... *A61K 31/755* (2013.01); *A61K 9/0014* (2013.01); *A61K 9/0043* (2013.01); *A61L 2/23* (2013.01); *A61L 2101/46* (2020.08); *A61L 2202/20* (2013.01)

(58) Field of Classification Search
CPC ................................. A61K 31/755
See application file for complete search history.

(56) References Cited

U.S. PATENT DOCUMENTS

| 4,010,259 | A | 3/1977 | Johansson |
| 4,381,380 | A | 4/1983 | LeVeen et al. |
| 4,999,190 | A | 3/1991 | Fina |
| 2014/0217037 | A1 | 8/2014 | Theivendian et al. |

FOREIGN PATENT DOCUMENTS

| WO | 2010033258 A1 | 3/2010 |
| WO | 2010124130 A2 | 10/2010 |

OTHER PUBLICATIONS

Luo et al., "Antimicrobial Activity and Biocompatibility of Polyurethane-Iodine Complexes." Journal of Bioactive and Compatible Polymers, vol. 25, No. 2, Mar. 2010, pp. 185-206.
Yue et al.,. Adv. Funct. Mater. 2015, 25, 6756-6767.
Dolez et al., JOSE 2009, vol. 15, No. 4.

*Primary Examiner* — Benjamin J Packard
(74) *Attorney, Agent, or Firm* — Aileen Law; Oppedahl Patent Law Firm LLC

(57) ABSTRACT

Disclosed is a method and apparatus for using iodinated polymer as an antimicrobial agent to manage the suppression and disinfection of pathogens.

10 Claims, 4 Drawing Sheets

Figure 4

| Wuxi Apptec Laboratory Reports | Pseudomonas[1] aeruginosa – Log Reduction | Staphylococcus aureus- Log Reduction | Contact times |
|---|---|---|---|
| Final Report 824050.pdf | > 6.0 | | 0, 5 (min.) |
| Final Report 823395 (2).pdf | > 5.9 | > 4.6 – 6.2 | 0, 2, 5, 15 (min.) |
| Final Report 822668.pdf | > 6.5 | > 5.0 | 0, 2, 5, 15 (min.) |
| 901978.pdf | > 6.3 | | 0, 24, 48, 72, 96 (hrs.) |
| 831569.pdf | > 6.1 | | 0, 72 (hrs.) |
| 829684 | > 5.6 | | 0, 2, 5, 15 (min.) |
| 823213.pdf | > 4.3 | | 0, 24 (hrs.) |
| 793489.pdf | > 2.3, 5.0, 6.6, 6.2 | > 4.4, 5.1, 6.0, 6.2 | 0, 24, 48, 72 (hrs.) |

[1]Pseudomonas aeruginosa is considered an excellent model for evaluation of efficacy due to its ruggedness and its resistance to antimicrobial agents.

METHOD AND APPARATUS FOR USING IODINATED POLYMER AS AN ANTIMICROBIAL AGENT TO MANAGE THE SUPPRESSION AND DISINFECTION OF PATHOGENS

TECHNICAL FIELD

The present disclosure relates to an agent comprising polyiodide resin to provide or facilitate an immediate contact kill of bacterial, viral and fungal pathogens s. More specifically, the present method and apparatus provides for the application of an iodinated polymer on one or more devices to achieve a 4-log reduction of organisms such as viruses, bacteria, fungus, yeasts and molds to achieve antimicrobial suppression and disinfection.

BACKGROUND

With respect to antimicrobial suppression and disinfection procedures that are intended to protect humans or animals against disease or harmful biological agents, the efficacy of a product is measured by its log reduction, also commonly known as log kills. The term "log reduction" indicates a 10-fold reduction, which means that with every step, the number of bacteria present is reduced by 90 percent. For example, if there are one million bacteria present on a surface, a 1-log reduction would reduce the number of bacteria by 90 percent, or 100,000 bacteria remaining. A 2-log reduction removes 99 percent, leaving behind 10,000 bacteria, 3-log removes 99.9 percent to leave behind 1,000 bacteria, and so on. The present method and apparatus is capable of achieving a 4-log kill, removing 99.99 percent to leave behind 100 bacteria.

When speaking in terms of bacterial, viral and fungal pathogens, log reduction is very important because these organisms are numbered in the millions or more due to the rapid doubling time of microorganisms. Furthermore, with the prevalence of antibiotic resistance, antibiotics that once provided protection against these dangerous pathogens are no longer as effective.

The iodinated polymer agent disclosed herein—namely, polyiodinated resin particles—acts as an antimicrobial agent, an antiviral agent, a biochemical agent or a reducing agent which exerts a toxic effect on a diverse array of microorganisms and other pathogens and environmental toxins while not being toxic to the user.

The present apparatus and method has been shown to meet the FDA recommendation for coating of patient-care equipment, such as cystoscopes, catheters, thermometers, tubing, etc., exceeding the FDA 4-log reduction requirement for medical devices. However, it has been determined that the iodinated polymer agent can be mixed with various adhesives and other materials to form outer and internal coatings for specific applications in which one or more coated layers between surfaces can provide additional protection against pathogens.

The present apparatus and method has been shown to meet the FDA recommendation for manufacturers of delivery devices such as DPIs (Dry Product Inhalers), nebulizers or ventilators, demonstrating a 4 log reduction (through a combination of capture or destruction) of claimed particulates. In one embodiment, dry product was used, however it has been determined that the iodinated polymer can be mixed with aqueous solutions to form a nasal spray or nasal drops for use as a therapeutic treatment.

The iodinated polymer agent can also be mixed with charcoal as a therapeutic treatment in human and veterinary applications.

In addition, it has been demonstrated that the present apparatus and method meets the FDA 4-log reduction requirement for antimicrobial suppression and disinfection applied to PPE such as masks, covers, gloves, safety glasses, coats, sleeves, gowns, etc. In one embodiment, an imprinted coating process was employed, however, it is contemplated that an extrusion process be used to form face masks, gowns, surgical packs, covers and other protective devices by means of spun blown fibers/non-woven materials.

It has been determined that the iodinated polymer agent can be used in solution or as a solid dispersions to develop a foam for wound treatment or other topical applications. Similarly, the iodinated polymer agent can be used to develop a cream, lotion or gel to prevent infections in cuts and abrasions.

The present apparatus and method will also meet the FDA recommendation for manufacturers of air filtration upon the demonstration of a 4 log reduction of claimed particulates. Other applications of the iodinated polymer agent can include treatment of whole blood or blood fractions to extend shelf life and treatment of food container systems to inhibit or reduce spoilage. Furthermore, the iodinated polymer agent can be mixed with clay or other base materials to form a cat litter product that can minimize and reduce bacteria.

What is needed are apparatus capable of providing reliable protection for antimicrobial suppression and disinfection. The iodinated polymer agent disclosed herein—namely, polyiodinated resin particles—can be implemented in a variety of ways and with various media to exert a toxic effect on pathogens and environmental toxins while not being toxic to the user. The application of the present method and apparatus may have additional advantages since it can be implemented with to medical and non-medical products that do not necessarily need to meet the strict FDA 4-log reduction criteria.

SUMMARY OF THE DISCLOSURE

The disclosed device provides for the use of iodinated polymer as an antimicrobial agent to manage the suppression and disinfection of pathogens.

The disclosed device provides for a polyiodide resin-enhanced apparatus which creates a molecular sub-microscopic "cloud of protection" between the apparatus and the user.

The disclosed device provides for a polyiodide resin-enhanced apparatus that is capable of achieving a 4 log reduction of organisms.

The disclosed device provides for the preparation of an iodinated polymer with an adhesive to form a polyiodide resin-enhanced coating comprising up to about 10% by weight of added polymer.

The disclosed device provides for the preparation of a polyiodide resin-enhanced nasal treatment comprising up to about 10% by weight of added polymer.

The disclosed device provides for the preparation of a polyiodide resin-enhanced therapeutic treatment comprising up to about 10% by weight of added polymer and further comprising charcoal.

The disclosed device provides for the preparation of a polyiodide resin-enhanced apparatus that utilizes extrusion spinning (i.e. spun bonded) to create PPE having a zone of inhibition or a protective barrier around the corresponding PPE.

The disclosed device provides for the preparation of a polyiodide resin-enhanced apparatus using extrusion spinning (i.e. spun bonded) to form a fiber textile product comprising up to about 10% by weight of added polymer to create PPE such as face masks, gowns, surgical packs, covers and other protective devices.

The disclosed device provides for the preparation of an iodinated polymer foam for wound treatment or other topical applications.

The disclosed device provides for the preparation of a topical agent such as a cream, lotion or gel comprising an iodinated polymer to prevent infections in cuts and abrasions.

The disclosed device provides for the preparation of an enhanced mechanical device such as air purifiers, air filtration canisters, aromatherapy diffusers, etc. comprising iodinated polymer particles.

The disclosed device provides for the application of a polyiodide resin powder in conjunction with whole blood or blood fractions to extend shelf life.

The disclosed device provides for the application of a polyiodide resin powder in conjunction food container systems to inhibit or reduce spoilage.

The disclosed device provides for the application of an iodinated polymer agent in conjunction with clay or other base materials to form consumer goods such as a cat litter product that have the ability to minimize and reduce bacteria.

BRIEF DESCRIPTION OF THE FIGURES

FIG. 4 Table of compiled data exhibiting contact times and effectiveness.

DETAILED DESCRIPTION OF THE DISCLOSURE

Definitions

Figure 1:
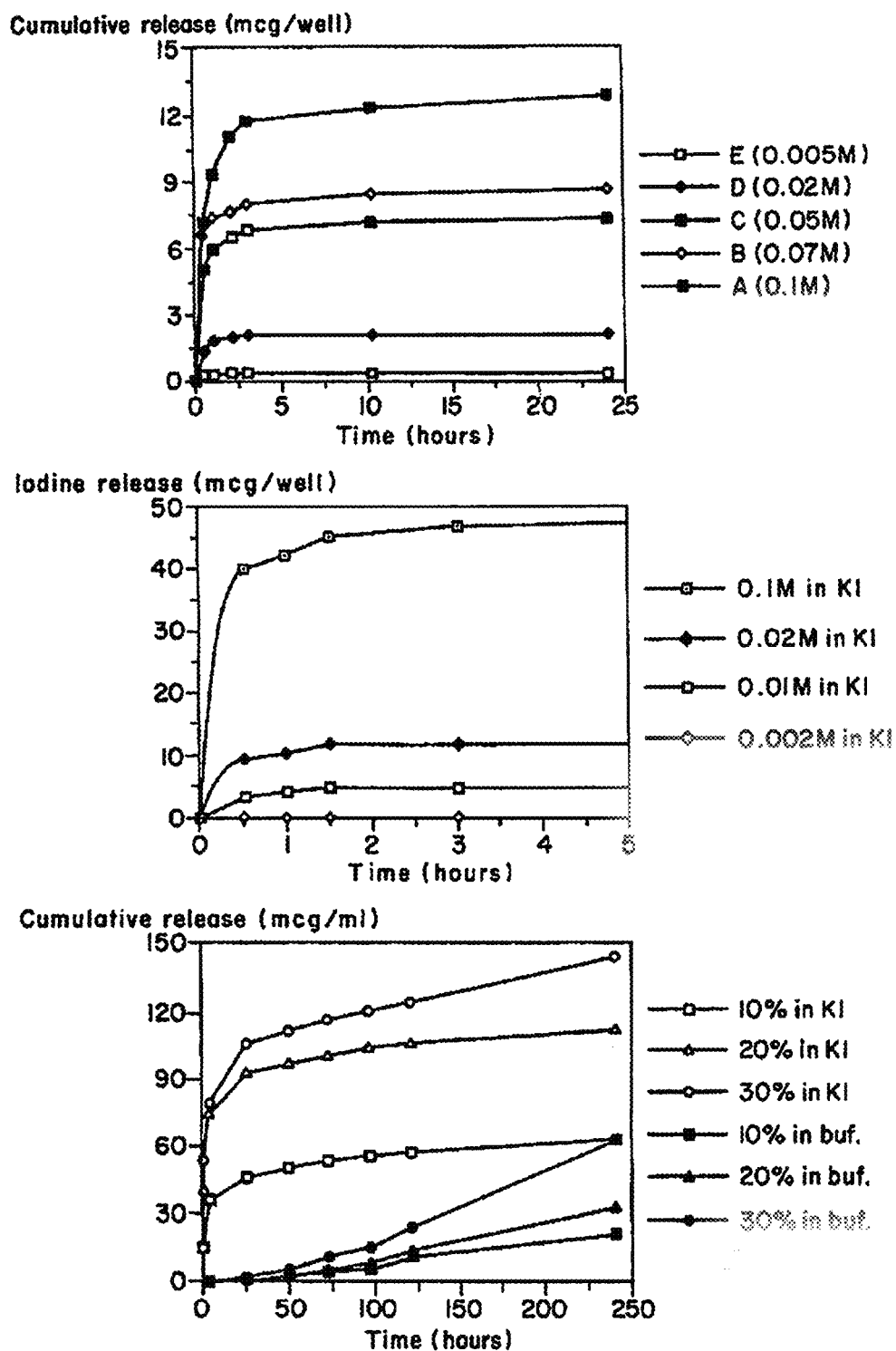
FIG. 1. Release rates from previous studies.
Figure 2:
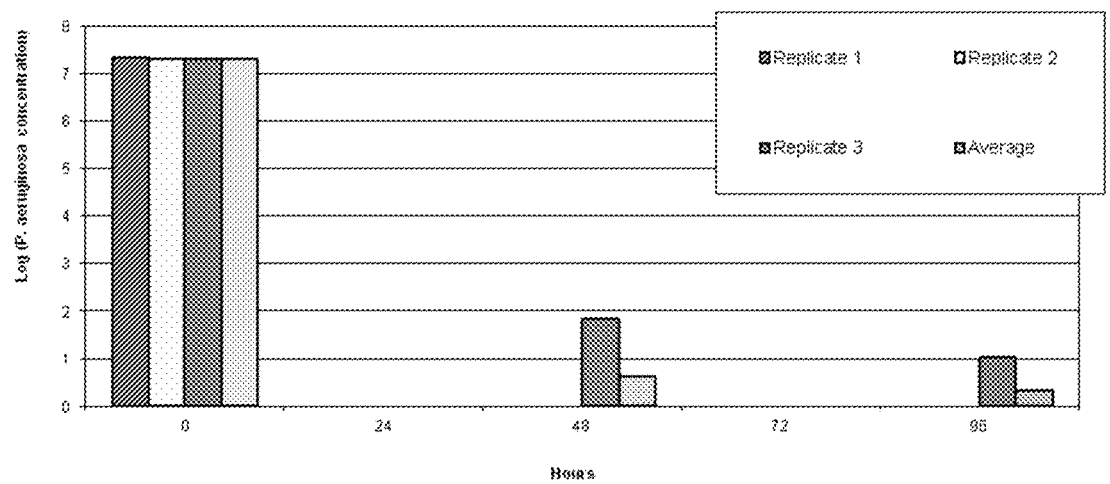
FIG. 2 Graph showing biological performance of latex/iodinated resin coated latex elastomers of the present disclosure against the challenge microorganism *Pseudomonas aeruginosa*, with re-inoculation every twenty-four hours (Report Number 901978).
Figure 3:
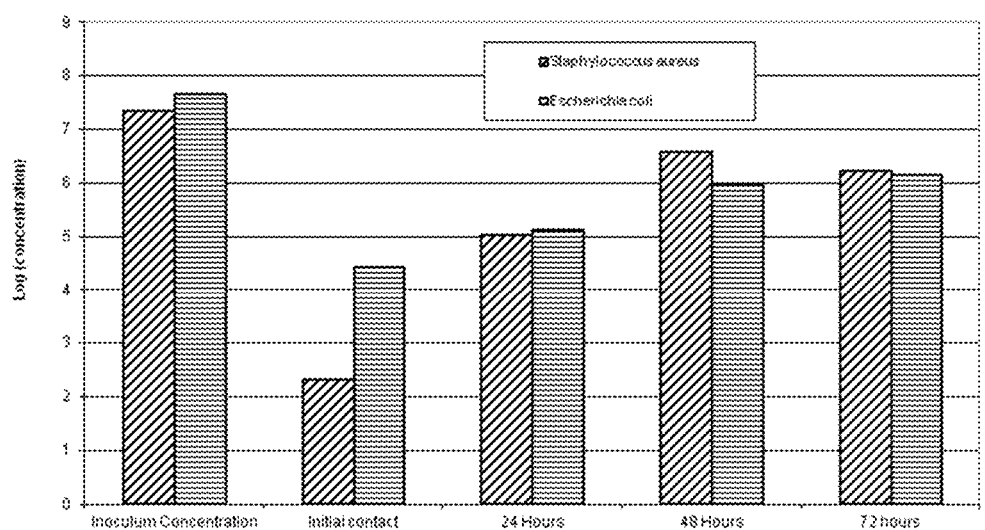
FIG. 3 Graph showing biological performance of latex/iodinated resin coated latex elastomers of the present disclosure against the challenge microorganisms *S. aureus* and *E. Coli* (Report Number 793489).

Polyiodide—Molecular iodide of more than one iodine atom containing a net negative charge
Antimicrobial—An agent that kills microorganisms or inhibits their growth.
Ion-Exchange—An exchange of ions between two electrolytes or the exchange of ions of the same charge between an insoluble solid and a solution in contact with it or an electrolyte solution and a complex or solid state material.
Biological Buffer—An organic substance that has a neutralizing effect on hydrogen ions.

Iodine is a well-known broad spectrum antimicrobial agent that has bactericidal, fungicidal and virucidal properties which has been used for over centuries as an antiseptic. When iodine is introduced into an aqueous solution, free iodine, which provides the germicidal effect, is released. While generally inhibiting infective germs over the short term, the biocidal effectiveness of iodine is dependent on, inter alia, how long the infective agent is exposed to it.

To increase the effectiveness of iodine, it is normally combined with a solubilizing agent or other carrier to form an iodophor. Such iodophors, in effect, provide a reservoir of iodine from which small amounts of free iodine in aqueous solution are released over a period of time. This iodophor formulated for example, as a solution, soap, cream or paste, and are then topically applied to that area of a patient's body which is desired to be treated. Perhaps the best known of these iodophors is povidone-iodine, in which iodine in the form of triiodide is complexed with the polymer polyvinylpyrrolidone. An example of such an application can be found by reference to U.S. Pat. No. 4,010,259.

Polyiodide resins have proven to be as much as 1,000,000 times more effective than an iodine ($I_2$) molecule alone. A large number of chemical, biochemical, and physiological studies have proven that the iodine added to microorganisms is irreversibly bound. This has the effect of devitalizing the microorganisms by damaging cellular proteins, lipids, enzymes, oxidation of sulfhydryl groups and other chemical pathways.

Microorganisms carry an electrical potential energy on their surface. The polyiodide resin carries an electrical potential charge which attracts the microorganisms. The microorganisms with their negative electrical potential are naturally drawn to the iodinated resin particles with their positive electrical potential charge and vice versa, thus ensuring contact and devitalization. The iodinated resin releases the correct lethal dose of nascent iodine in less than about 3 seconds at a body temperature of about 98.6° C. or about 36.9° C.

The ion-exchange resin bead or particle is chemically bonded homogeneously with polyiodide of uniform composition throughout its interior. As nascent iodine is consumed more is continuously fed to the surface from the interior of the resin bead or particle.

This creates an equilibrium of the resin $I_3$ to the natural release of $I_2$ into the immediate environment as follows:

$$\text{Resin-}I_3 \leftrightarrow \text{Resin-}I^- + I_2$$

$$\text{Resin-}I_5 \leftrightarrow \text{Resin-}I_3 + I_2 \leftrightarrow \text{Resin }I^- + I_2 + I_2$$

$$\text{Resin-}I_7 \leftrightarrow \text{Resin }I_5 + I_2 \leftrightarrow$$

$$\text{Resin }I_3 + I_2 + I_2 \leftrightarrow \text{Resin }I^- + I_2 + I_2 + I_2$$

By enabling effective disinfection and/or sterilization of the immediate environment at or on the surface of a target apparatus, the disclosed method and device provides a zone of inhibition as a protective barrier around the corresponding PPE. This provides for a molecular sub-microscopic "cloud of protection" between the equipment and the user.

The unique release on demand feature of polyiodide resin can be demonstrated by adding resin beads to the well of a depression microscope slide with a suspension of the highly Motile Ciliate Tetrahymena Pyriforms. When observed microscopically, individual cells maintain their motion while swimming in a solution with 2 ppm of iodine residual. However after a collision with a resin bead, their activity dramatically slows and within seconds stops altogether.

Bacteria, viruses, yeast, fungi, and protozoa are not able to develop resistance to iodine even after a period of prolonged exposure to polyiodinated resins. It is not expected that emerging new infections will develop resistance to iodine, as historically there has been no development of resistance to iodine, as well as polyiodinated resin.

The iodinated polymer agent disclosed herein—namely, polyiodinated resin particles—can be implemented in a variety of ways and with various media to exert a toxic effect on pathogens and environmental toxins while not being toxic to the user.

The particle sizes of the polyiodinated powders disclosed herein can range from about 1 micron to about 150 microns. In some embodiments, the particle sizes range from about 5 microns to about 10 microns. Alternative sources of the polyiodinated resins may be used subject to meeting the same purity and physical conditions. Iodinated resins used in accordance with the present disclosure are referred to as polyiodinated resin.

The base polymer used to manufacture such polyiodinated resins is a strong base anion exchange resin. These resins contain quaternary ammonium exchange groups which are bonded to styrene divinylbenzene polymer chains. Polyiodinated resins can be made with different percentages of iodine and may be used in accordance with the present disclosure. Different percentages of iodine in the polyiodinated resins will confer different properties to the resin, in particular, different levels of biocidal activity. The particular resin used is based on the desired application.

A significant advantage of the present disclosure is that a relatively small amount of the antimicrobial agent need be applied in order to exert a significant toxic effect on a broad spectrum of pathogens.

With regards to efficacy, the present system has been tested against a robust organism *Pseudomonas aeruginosa* utilizing the following recognized standards: AATCC Method 100 (modified for twenty-four hour repeat insult testing) and ASTM E2149 (modified for twenty-four hour repeat insult testing). The test results showed an average reduction of greater than $10^6$ in bacterial count vs. untreated samples).

As there was no testing protocol available to demonstrate the efficacy of the disclosed device as it relates to its kill capabilities, the time involved, and its long term efficacy, specific test protocols were developed in relation to the disclosed device. It is well-known in the industry of life sciences, testing protocols provide individual sets of instructions that allow for the recreation of a particular laboratory experiment. Protocols provide instructions for the design and implementation of experiments that include the safety bias, procedural equipment, statistical methods, reporting and troubleshooting standards for experiments.

As disclosed herein, modifications were made to standardized test criteria (AATCC method 100 and ASTM E2149) which resulted in the development of specific protocols that allow for the evaluation and testing of the killing capability of the disclosed device over an extended time period of up to 96 hours and beyond. The modifications consisted of the use of ASTM E2149 as the base testing protocol along with AATCC method 100 applied to multiple 24-hour nonstop testing of the original sample versus a single 24-hour test period as prescribed by AATCC 100.

By way of background, the AATCC 100 test method evaluates the antibacterial properties of textiles over a 24-hour period of contact, quantitatively assessing bacteriostatic (growth inhibition) properties or bactericidal (killing of bacteria) properties associated with a textile. The method ensures continuity in approaches and replicability of results.

The ASTM E2149 method, titled "Determining the Antimicrobial Activity of Immobilized Antimicrobial Agents under Dynamic Contact Conditions" is a sensitive test. It is often used to measure the antimicrobial activity of non-leaching, irregularly shaped or hydrophobic surfaces.

With regards to efficacy, the present system has been tested against a robust organism *Staphylococcus aureus* utilizing the following recognized standards: AATCC Method 100 (modified for twenty-four hour repeat insult testing). The test results showed an average reduction of greater than $10^6$ in bacterial count vs. untreated samples).

As an example, a horse having late stage pneumonia that was expected to expire within 24 hours was treated with the disclosed dry powder and was within 24 hours healthy and pneumonia free.

The powder demand release antimicrobial contact disinfectant polyiodinated resin has been proven to maintain its kill capabilities beyond 96 hours (repeated inoculation every 24 hours with $>10^7$ *Pseudomonas aeruginosa* for the entire study) as referenced by test results done by Wuxi AppTec, a third party reference lab. The antimicrobial powder is capable of providing a high level of protection against microbes and other many biohazards, such as viruses, bacteria, fungi, and molds. In the disclosed embodiment, the polyiodinated resin particles advantageously have an average size within the range from about 5 μm to about 10 μm.

As disclosed, the polyiodide resin powder begins with a pure cationic resin which is commercially available as a chloride (Cl$^-$) as the anion. The anion exchange resin may be a whole series of possible polymers that are carbon based, but in the disclosed embodiment, the resin used is a commercially available styrene-divinylbenzene copolymer resin that has a quaternary ammonium cation as an integral part of the resin matrix. This can be described as resin with nitrogen (N) and carbon-based residues (R) attached to the resin, with the property of having a resin with a positive charge and a counter anion (Cl$^-$) with a negative charge, to end up as a neutral complex.

Typically, anion exchange resins are in the form of hydroxide (OH$^-$) or chloride (Cl$^-$). The hydroxide form can be further reacted with hydrochloric acid to form the chloride version of the resin as follows:

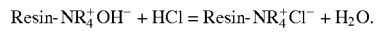

This is further reacted in the presence of Iodine (I$_2$ as a mineral) and Iodide (I$^-$) salt (sodium or potassium iodide) to allow for the formation of I$_3^-$, I$_5^-$, and I$_7^-$. The initial reaction is [I$_2$+I$^-$=I$_3^-$], which upon excess I$_2$ will react further to form I$_5^-$ as in [I$_2$+I$_3^-$=I$_5^-$], and which upon additional excess I$_2$ will react further to form I$_7^-$ as in [I$_2$+I$_5^-$=I$_7^-$]. This is now referred to as the polyiodide resin in the disclosed system. Reactions are as follows:

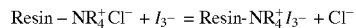
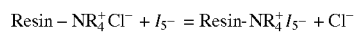
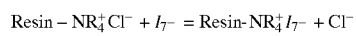

Various ratios of chemicals are combined to optimize the formation of the polyiodide versions above by adding an excess of the I$_2$ and I$^-$ in appropriate proportions to substitute out the Cl$^-$ or other anions or halides based on the stoichiometry (ratio) of the reactants as given above. Multiple routes from chromatography to reactor pressures and heated fluid beds may be used to realize the end product in accordance with well-known manufacturing processes, with the variables of pressure, temperature and ratios.

The reactor operates at elevated temperatures of above room temperature to the limits of the resin's thermal stability profile temperature and at pressures of one or more atmospheres of pressure. The process can be optimized to produce a batch of any size (subject to the reactor vessel size) in a matter of hours or within one day. The total weight of iodine in the polyiodinated resin formed from the process ranges about 45% to about 70% by weight of the polyiodide complex depending on the introduction of $I_3^-$, $I_5^-$, and/or $I_7^-$. By careful control of the ratios of the Resin based Chloride version of the resin and the $I_2$ and $I^-$ ratios, mixtures ranging from the $I_3^-$ through the $I_7^-$ versions and mixtures in between can be produced. Careful control of specific ratios of reactants can yield specific versions, but are typically reaction mixtures favoring one of the polyiodides over the others. For example, if $I_3^-$ is introduced, the resulting polyiodinated resin comprises about 45% by weight of the polyiodide complex. If $I_5^-$ is introduced, the resulting polyiodinated resin comprises about 62% (by weight of the polyiodide complex. If $I_7^-$ is introduced, the resulting polyiodinated resin comprises about 69% by weight of the polyiodide complex.

The resulting polyiodide resin is then ground to about 5 μm to about 10 μm thereby forming the polyiodide resin powder. Yields at or near 100% are possible, but typically due to manufacturing loses and limits may be less than 100%.

Buffering agent can be added to maintain the desired pH, subject to the specific buffering agent that is used, in a ratio that allows for the control of the pH of the mixture in a wet environment (such as tissue or lungs) to be in the range of 3 to 7 pH units. Although any ratio of polyiodide to buffering agent can be used in the range of 10% to 100% of the polyiodide, typically the dominate agent is the polyiodide in the range of 50% to 100% of the total of the combined materials of the polyiodide styrene-divinylbenzene copolymer resin and the buffer agent.

Some examples for medical grade buffering agents that may be used are 4-(2-hydroxyethyl)-1-piperazineethanesulfonic acid (HEPES), 2-(N-morpholino)ethanesulfonic acid (MES), 3-(N-morpholino)propanesulfonic acid (MOPS) and citrates, however others may be suitable.

Tested organisms comprise *Pseudomonas aeruginosa* and *Staphylococcus aureus*. Test results for SARS (SARS-CoV-1) and Coronavirus (SARS-CoV-2) are expected to be better compared to the most robust *Pseudomonas aeruginosa* and *Staphylococcus aureus*.

The present disclosure describes various ways in which the subject polymer resin particles can be implemented. In each embodiment, the disclosed device was capable of demonstrating a 4 log reduction of organisms. The polyiodinated resin is capable of being tailored to specific medical needs based on the iodine concentration of iodine in its various forms such as $I_3^-$, $I_5^-$, $I_7^-$.

For example, the polyiodide resin powder can be mixed with an adhesive to form a coating for specific applications. In one contemplation, the iodinated polymer disclosed herein would be mixed with cyanoacrylate to form an outer coating comprising up to ten percent (10%) by weight of added polymer for medical gloves. Furthermore, the iodinated polymer agent can be used to form a coated layer to provide additional protection against pathogens, for example, between layers of gauze and other wound dressings or in glove substrate. It will be recognized however by one having ordinary skill in the art that suitable adhesives such as acrylates, polyurethane, epoxy resins, etc. may be selected for specific applications.

In another contemplation, the iodinated polymer can be mixed with aqueous solutions to form a nasal spray or nasal drops for use as a therapeutic treatment. Formulations comprising up to about ten percent (10%) by weight of added polymer could be based in water, saline or similar aqueous solutions. It will be recognized by one having ordinary skill in the art that other polymer concentrations may be appropriate as desired for specific applications.

One preparation method of a polyiodinated nasal treatment comprises the steps of:

reacting a cationic resin having a positive charge and an anion having a negative charge in the presence of iodine (I2 as a mineral) and Iodide (I−) salt (sodium or potassium iodide) to allow for the formation of I3−, I5−, and I7− thereby forming a polyiodide resin having a total weight of iodine ranging from about 45% to about 70% by weight of polyiodide complex depending on the introduction of I3−, I5−, and/or I7−;

processing said polyiodide resin to form a polyiodide resin powder having a mesh size of about 1 μm to about 150 μm; and dissolving said resin powder in purified water for a specified period of time to form an aqueous solution, whereby said aqueous solution can be introduced into a nasal passage for therapeutic purposes.

Similarly, the iodinated polymer agent can also be mixed with charcoal as a therapeutic treatment in human and veterinary applications.

In a previous embodiment, the present apparatus and method was shown to meet the FDA 4-log reduction requirement for antimicrobial suppression and disinfection applied to PPE such as face masks, gowns, surgical packs, covers and other protective devices by means of depositing a printable polyiodide ink onto or into one or more surfaces of PPE. It is been determined that other processes, such as using an extrusion process implementing spun blown fibers/non-woven materials, are viable.

Extrusion spinning (i.e. spun bonded) or melt spinning is a spinning technique where polymer is extruded by a spinneret. Usually, the polymer is fed into the spinning machine in pellet or chip form, melted and then pressed through. In one embodiment, the iodinated polymer may be introduced into the extrusion process as a raw material to be direct spun to eliminate the step of feeding the polymer in as pelletized or chipped feedstock. After being extruded by the spinneret, the iodinated polymer solidifies into a yarn-shaped product. A feedstock of molded thermoplastic polymer comprising up to up to about ten percent (10%) by weight of added polymer could be combined with polyethylene, polypropylenes, acrylates and other thermoplastics. It will be recognized by one having ordinary skill in the art that other polymer concentrations as well as other materials may be appropriate as desired for specific applications.

One method of providing polyiodide resin powder-enhanced personal protective equipment (PPE) capable of creating a protective barrier around the PPE for a direct contact kill of bacteria, fungi and viruses, the method comprising the steps of:

reacting a cationic resin having a positive charge and an anion having a negative charge in the presence of iodine (I2 as a mineral) and Iodide (I−) salt (sodium or potassium iodide) to allow for the formation of I3−, I5−, and I7− thereby forming a polyiodide resin having a total weight of iodine ranging from about 45% to about 70% by weight of polyiodide complex depending on the introduction of I3−, I5−, and/or I7−;

processing said polyiodide resin to form a polyiodide resin powder having a mesh size of about 1 µm to about 150 µm; and introducing said polyiodide resin powder into an extrusion process (i.e. spun bonded) as a feedstock to be direct spun to form a fiber textile product capable of being used to create a polyiodide resin-enhanced PPE apparatus that enables sub-microscopic protection between the apparatus and a user.

Disclosed herein, the iodinated polymer agent can be used in solution or as a solid dispersion to develop a foam for wound treatment or other topical applications. Similarly, the iodinated polymer agent can be used to develop a cream, lotion or gel to prevent infections in cuts and abrasions. In one embodiment, a formulation comprises up to about ten percent (10%) by weight of added polymer to a gel, for example a carbomer-based or hydrophilic cellulose-based gel.

One preparation method for the polyiodinated gel comprises the steps of:

reacting a cationic resin having a positive charge and an anion having a negative charge in the presence of iodine (I2 as a mineral) and Iodide (I−) salt (sodium or potassium iodide) to allow for the formation of I3−, I5−, and I7− thereby forming a polyiodide resin having a total weight of iodine ranging from about 45% to about 70% by weight of polyiodide complex depending on the introduction of I3−, I5−, and/or I7−;

processing said polyiodide resin to form a polyiodide resin powder having a mesh size of about 1 µm to about 150 µm;

dissolving a carbomer in purified water for a specified period of time to form a gel; and mixing said polyiodide resin powder with said gel to create a polyiodide resin-enhanced topical agent.

Not only are liquid-based forms of lotions or creams which comprise, for example, aloe, lanolin, carbomer, hydrophilic cellulose, and others, within the scope of the disclosure, it is contemplated that the iodinated polymer can be directly added to monomer materials to form liquid foams or solid powders that can be polymerized or otherwise solidified to form solid foams as in the case of urethane or polyvinyl alcohol solid foams.

As stated herein, the present apparatus and method is capable of meeting the FDA recommendation of a 4 log reduction of pathogens, and as such it is contemplated that the polyiodide resin disclosed herein could be used to enhance mechanical devices such as air purifiers, air filtration canisters, aromatherapy diffusers, etc. In these types of devices, larger polymer particles could be used as deemed practical. For example, it is contemplated that a filtration system canister could contain up to ninety-nine percent (99%) or higher of the canister volume of polymer.

The polyiodide polymer could even have a broader application outside of medical uses. For example, in some cases, it may be useful in shelf life programs to treat whole blood or blood fractions with the polymer to extend shelf life, or food container systems to inhibit or reduce spoilage.

In yet another contemplation, the iodinated polymer agent may be useful when mixed with clay or other base materials to form consumer goods such as a cat litter product that can minimize and reduce bacteria.

As disclosed herein, the present method and apparatus is capable of achieving a 4-log reduction of organisms to meet FDA standards/recommendations. However, the use of the present method and apparatus that do not necessarily have to meet the FDA 4-log reduction criteria may nonetheless be advantageous and can have broader applications outside of medical uses.

The invention claimed is:

1. A preparation method for a polyiodinated therapeutic treatment, the method comprising the steps of:
   reacting a cationic resin having a positive charge and an anion having a negative charge in the presence of iodine (I2 as a mineral) and Iodide (I—) salt to allow for the formation of I3-, I5-, and I7- thereby forming a polyiodide resin having a total weight of iodine ranging from about 45% to about 70% by weight of polyiodide complex depending on the introduction of I3-, I5-, and/or I7-;
   processing said polyiodide resin to form a polyiodide resin powder having a mesh size of about 1 µm to about 150 µm; and
   dissolving said polyiodide resin powder in an aqueous solution for a specified period of time to form a polymer-enhanced solution comprising up to about 10% by weight of added polymer, whereby said polymer-enhanced solution can be administered to a patient for therapeutic purposes.

2. The method of claim 1, wherein the dissolving step further comprises adding a concentration of charcoal to said polymer-enhanced solution comprising up to about 10% by weight of added polymer.

3. A method of providing polyiodide resin powder-enhanced personal protective equipment (PPE) capable of creating a protective barrier around the PPE for a direct contact kill of bacteria, fungi and viruses, the method comprising the steps of:
   reacting a cationic resin having a positive charge and an anion having a negative charge in the presence of iodine (I2 as a mineral) and Iodide (I—) salt to allow for the formation of I3-, I5-, and I7- thereby forming a polyiodide resin having a total weight of iodine ranging from about 45% to about 70% by weight of polyiodide complex depending on the introduction of I3-, I5-, and/or I7-;
   processing said polyiodide resin to form a polyiodide resin powder having a mesh size of about 1 µm to about 150 µm; and
   introducing said polyiodide resin powder into an extrusion process as a feedstock to be direct spun to form a fiber textile product comprising up to about 10% by weight of added polymer that is capable of being used to create a polyiodide resin-enhanced PPE apparatus that enables sub-microscopic protection between the apparatus and a user.

4. A method of preparing a topical treatment for wound care or preventative applications, the method comprising the steps of:
   reacting a cationic resin having a positive charge and an anion having a negative charge in the presence of iodine (I2 as a mineral) and Iodide (I—) salt to allow for the formation of I3-, I5-, and I7- thereby forming a polyiodide resin having a total weight of iodine ranging from about 45% to about 70% by weight of polyiodide complex depending on the introduction of I3-, I5-, and/or I7-;
   processing said polyiodide resin to form a polyiodide resin powder having a mesh size of about 1 µm to about 150 µm; and dissolving a carbomer in an aqueous solution for a specified period of time; and mixing said carbomer solution with said polyiodide resin powder to form create a polyiodide resin-enhanced topical agent comprising up to about 10% by weight of added polymer and capable of being used on a patient.

5. The method of claim 4, wherein the forming of said topical agent results in a gel comprising up to about 10% by weight of added polymer.

6. The method of claim 4, wherein the forming of said topical agent results in a lotion or cream comprising up to about 10% by weight of added polymer.

7. The method of claim 4, wherein the forming of said topical agent results in a foam comprising up to about 10% by weight of added polymer.

8. The method of claim 4, wherein the forming of said topical agent further comprises the step of adding a monomer to create a foam comprising up to about 10% by weight of added polymer.

9. A method of managing the suppression and disinfection of pathogens, comprising: administering an effective amount of the composition prepared in claim 1 into a nasal passage of a patient either directly or indirectly.

10. A preparation method for a polyiodinated therapeutic treatment, the method comprising the steps of:

reacting a cationic resin having a positive charge and an anion having a negative charge in the presence of iodine (I2 as a mineral) and sodium or potassium iodide to allow for the formation of I3-, I5-, and I7- thereby forming a polyiodide resin having a total weight of iodine ranging from about 45% to about 70% by weight of polyiodide complex depending on the introduction of I3-, I5-, and/or I7-;

processing said polyiodide resin to form a polyiodide resin powder having a mesh size of about 1 μm to about 150 μm; and dissolving said polyiodide resin powder in an aqueous solution for a specified period of time to form a polymer-enhanced solution comprising up to about 10% by weight of added polymer, whereby said polymer-enhanced solution can be administered to a patient for therapeutic purposes.

* * * * *